United States Patent [19]

Lewis et al.

[11] 4,176,232

[45] Nov. 27, 1979

[54] SULFONIC ACID SALTS OF ACYLOXYALKYLAMINES

[75] Inventors: Sheldon N. Lewis, Willow Grove; Jerome F. Levy, Dresher, both of Pa.

[73] Assignee: Rohm and Haas Company, Philadelphia, Pa.

[21] Appl. No.: 740,480

[22] Filed: Jun. 27, 1968

[51] Int. Cl.² ............................................. C07C 69/54
[52] U.S. Cl. ..................................... 560/222; 560/193; 560/195; 560/196; 560/84; 560/85; 560/87; 560/88
[58] Field of Search ................ 260/486; 560/222, 193, 560/195, 196, 84, 85, 87, 88

[56] References Cited

U.S. PATENT DOCUMENTS

| | | | |
|---|---|---|---|
| 2,677,699 | 5/1954 | Barney | 260/486 |
| 2,923,734 | 2/1960 | Sheetz | 260/486 |
| 3,024,221 | 3/1962 | Le Fevre et al. | 260/486 X |
| 3,359,305 | 12/1967 | Sheetz | 260/486 |

Primary Examiner—Paul J. Killos
Attorney, Agent, or Firm—Terence P. Strobaugh; George W. F. Simmons; Robert A. Doherty

[57] ABSTRACT

A sulfonic acid salt of an acyloxyalkylamine is prepared by reaction of an organic acid or amino-acid with a sulfonic acid salt of an alkanolamine. Isocyanates are prepared therefrom by reaction with phosgene.

8 Claims, No Drawings

SULFONIC ACID SALTS OF ACYLOXYALKYLAMINES

This invention relates to the production of novel sulfonic acid salts of acyloxyalkylamines (ester amine sulfonic acid salts) and the corresponding isocyanates therefrom.

The ester amine sulfonic acid salts of the present invention are valuable intermediates in the preparation of other compounds. They are of particular use in preparing isocyanates by phosgenation. The ester amine sulfonic acid salts, especially of polymerizable carboxylic acids, are of considerable interest in the preparation of polycationic polymers, particularly as a source of poly-primary-amino functionality. The dibasic acyloxyalkylamine sulfonic acid salts may also be used as curing agents for epoxy resins, either directly as the sulfonic acid salt or as the hydrochloride salt to which the sulfonic acid salt is readily convertible.

In copending U.S. patent applications Ser. Nos. 518,977 and 519,001, both filed Jan. 6, 1966, there is disclosed the preparation of hydrochloride salts of ester amines by means of direct esterification of saturated carboxylic or aminoacids with alkanolamine hydrochlorides in the presence of an excess of hydrogen chloride. Further disclosed is the conversion of the hydrogen chloride salts to isocyanates by reaction with phosgene. The above applications, which are in the hands of a common assignee and which are herein incorporated by reference, disclose processes which are a significant advance over the prior art; however, there are instances where the hydrochloride route is not suitable, either because the desired ester amine salt is produced in low yield or because a large amount of by products result.

The acyloxyalkylammonium sulfonate salt process of the present invention is particularly useful in preparing unsaturated esters of alkanolamine salts, such as the acrylic and methacrylic esters, from the unsaturated acids. In the case of the hydrogen chloride route significant amounts of by products, with unsaturated acids, are obtained because the hydrogen chloride tends to add across the unsaturation in the molecule. The sulfonate salt process of the present invention is also useful with a wide range of other organic acids and aminoacids, disclosed in more detail hereinafter, and generally gives much faster esterification rates at stoichiometric ratios of the alkanolamine salt and carboxylic acid reactants than any other known prior art procedure. Also, it has been found that there is improved mutual solubility of the alkanolamine sulfonic acid or sulfonate salt and the carboxylic acid reactants (as compared with the hydrochloride salt route) especially in the presence of an excess of sulfonic acid, and lower volatility of the sulfonic acid, thereby reducing losses and permitting the use of smaller excesses of acid. These advantages are particularly important from the standpoint of avoiding the use of an excess of one or the other reactants, thus by-passing steps such as isolation and purification of the intermediate amine salts prior to phosgenation to the isocyanate. The low sulfonate nucleophilicity in the instant invention also minimizes the decomposition or displacement of sensitive functional groups during the phosgenation reaction.

Now, in accordance with the instant invention, a process has been found for the direct esterification reaction of a free acid, an amino acid (or lactam) and an alkalolamine sulfonic acid salt to produce the corresponding acyloxyalkylamine (ester) sulfonic acid salts. In preparing the ester amine sulfonic acid salt in accordance with the instant invention, the alkanolamine is first converted to its acid salt. The resulting alkanolamine sulfonic acid salt is then reacted with the carboxylic acid reactant preferably in the presence of an inert liquid or diluent. The carboxylic acid reactant and the alkanolamine sulfonate and sulfonic acid when present in excess must have a significant solubility in each other under reaction conditions or else the inert liquid used as the reaction medium must be a mutual solvent for these materials. Where one of the reactants is a liquid or is molten under the reaction conditions, an excess of such reactant may be used as the reaction medium so long as such excess does not cause polymerization or promote other undesirable side-reactions, i.e., such excess must act as an inert liquid.

At room temperature, the reaction between the materials is too slow to be of practical significance. Generally, the reaction is carried out between about 40° C. and a temperature not higher than that at which the alkanolamine sulfonic acid salt dissociates into the free amine under the conditions used (i.e. of pressure and other reactants present in the mixture). Generally, the reaction temperature will be from about 50° C. to 200° C. and will be carried out in the presence of free excess sulfonic acid. Water is removed as the reaction progresses as by distillation with a liquid such as benzene which forms an azeotrope with the water. Generally, atmospheric pressure is preferred, but pressures either higher or lower than atmospheric may be used. Preferably, the pressure is chosen so as to have the diluent at its boiling point at the temperature used. Diluent need not necessarily be used; however, the esterification usually proceeds faster and goes further towards completion when the diluent is present. Suitable diluents or liquid reaction media include aromatic hydrocarbons, chlorinated hydrocarbons, chlorinated aliphatic hydrocarbons, chlorinated alicyclic hydrocarbon, etc. As specific examples, there may be mentioned toluene, benzene, xylene, ethylene dichloride, etc. Water also can serve as a convenient reaction media.

The comments above with respect to the carboxylic acid reactant also apply to the amino acid reactant and amino acid forming reactants (i.e., lactams), except that the amino acid reactant is converted to its sulfonic acid salt prior to the esterification reaction with the alkanolamine salt reactant. In the esterification process, the alkanolamine component and the acid or amino acid component may be used in stoichiometric equimolar amounts, or either component may be used in excess.

In schematic form, and for illustrative purposes only, there is shown below in Scheme I, the general reaction outline involving an acid and an alkanolamine salt, and the subsequent phosgenation to the corresponding isocyanate, in this case, 2-isocyanatoethyl methacrylate:

Scheme I $$CH_2=\underset{\underset{\displaystyle CH_3}{|}}{C}-CO_2H \; + $$

(I);

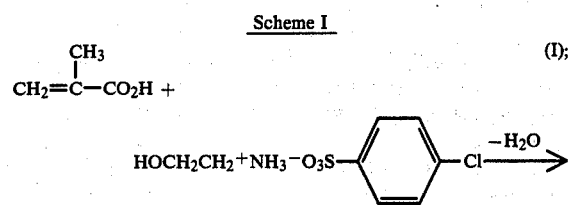

-continued
Scheme I

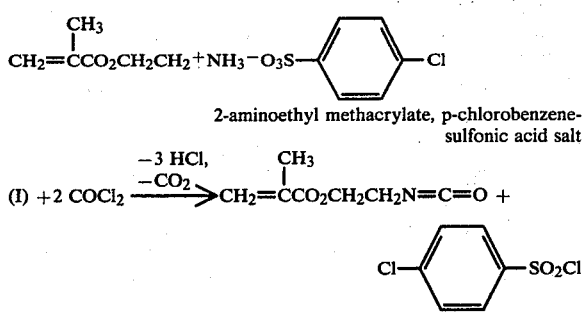

2-aminoethyl methacrylate, p-chlorobenzene-
sulfonic acid salt (I) +2 COCl₂ $\xrightarrow[-CO_2]{-3 HCl,}$ CH₂=C(CH₃)CO₂CH₂CH₂N=C=O +

Cl—⟨benzene⟩—SO₂Cl

In the reaction scheme denoted as Scheme II, there is shown below, again for illustrative purposes only, the general reaction involving an amino acid, in its sulfonic acid salt form, with the alkanolamine salt, and subsequent phosgenation to the corresponding isocyanate, in this case, 2-isocyanatoethyl 6-isocyanatocaproate.

Scheme II

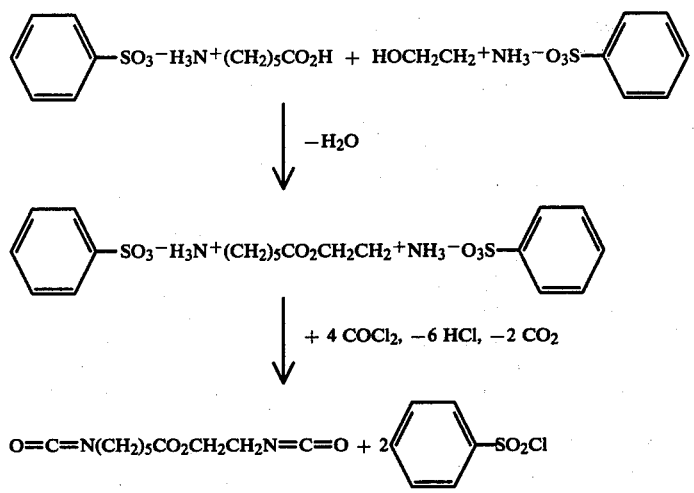

The alkanolamines which may be used in the instant invention contain from 2 to 8 carbon atoms, have one primary or secondary hydroxyl group and are primary amino group, and may include one oxygen or sulfur atom in the alkyl chain. The alkyl group of the alkanolamine may be substituted with an inert substituent group as alkyl, phenyl, nitro, halogen, etc. Particularly preferred alkanolamines are ethanolamine, (2-aminoethanol), 2-(2-aminoethoxy)-ethanol, 1-amino-2-propanol, 2-amino-1-propanol, 2-methyl-2-amino-1-propanol, 3-amino-1-propanol, and 2-amino-1-butanol. The ability of the present process to economically utilize a variety of alkanolamines permits the production of a variety of acyloxyalkylamine sulfonic acid salts wherein the amine group may be attached to a carbon which can be primary, secondary or tertiary. The isocyanates produced from these products will, in turn, offer a wide range of reactivities.

The sulfonic acids which are useful in the present invention include the commonly available alkyl, cycloalkyl, alkaryl, and aralkylsulfonic acids, and the halogen substituted alkyl, cycloalkyl, alkaryl and aralkylsulfonic acids, particularly chlorine substituted. Representative examples of useful sulfonic acids, include alkanesulfonic acids such as methanesulfonic acid, ethanesulfonic acid, etc., benzenesulfonic acid, napthalenesulfonic acid, p-chlorobenzenesulfonic acid, 2,5-dichlorobenzenesulfonic acid, 3,4-dichlorobenzenesulfonic acid, and the toluene sulfonic acids, ortho, meta and para. Alternatively, the sulfonic acids may be formed in situ in the reaction media by starting with the corresponding sulfonyl chlorides, for example, benzenesulfonyl chloride, and hydrolyzing them to the corresponding sulfonic acids.

The organic acids which may be reacted directly with the said alkanolamines in the process of the invention are dicarboxylic or dibasic acids having at least two carbon atoms, e.g., oxalic acid, succinic acid and dibasic acids wherein the two carboxyl groups are separated by a divalent aliphatic or alicyclic or aromatic group, the divalent group having at least two and preferably three atoms between the carboxyl groups, one of which atoms may be a hetero atom. The following acids are illustrative of those which may be used in the present invention: benzoic acid, the toluic acids; aliphatic α,ω-dicarboxylic acids having at least five carbon atoms as glutaric, adipic, sebacic, etc.; alicyclic dicarboxylic acid as 1,4-cyclohexane-dicarboxylic acid; aromatic dicarboxylic acids as o-phthalic acid, isophthalic acid, terephthalic acid, diphenic acid, 4,4'-diphenic acid, the phenylene diacetic acids, and 2,7-naphthalenedicarboxylic acid and 1,1,3-Trimethyl-5-carboxy-3-(p-carboxyphenyl)indane; dibasic acids containing a hetero atom as dinicotinic acid, diglycolic acid, thiodiacetic acid, p,p'-oxydibenzoic acid, the thiodialkanoic acids produced by reacting hydrogen sulfide with two moles of an unsaturated acid such as acrylic, methacrylic, crotonic, cinnamic, etc.; and the thiodialkanoic acids produced by reacting sodium sulfide and an ester of a halogenated acid. The oxygen and selenium analogs of these thiodialkanoic acids can also be used. In addition to these general classes of acids which may be used, both oxalic and succinic acids have been found to be operable. Further, the acids may contain substituents which do not interfere with the reaction of this invention. Such substituents include, for example, alkyl groups, aromatic groups, halogen groups as fluorine, chlorine, etc., nitro groups, etc. Examples of such acids are α-butyl-glutaric acid, α-β-diethylsuccinic acid, p-chlorobenzoic acid, β-chloroglutaric acid, etc. In addition to the above mentioned organic acids, the present invention is especially useful with unsaturated acids, particularly, $\alpha,\beta$-unsaturated monocarboxylic acids and unsaturated dicarboxylic acids. Preferred unsaturated acids are acrylic acid, methacrylic acid, fumaric acid, maleic acid and other unsaturated acids mentioned in U.S. Pat. No. 2,718,516. The anhydrides of the various acids given above may also be used as the organic acid component in the present invention. Preferred anhydrides are phthalic anhydride and maleic anhydride.

The amino acids which are useful in the invention are the monoamino-monocarboxylic acids, the monoamino-dicarboxylic acids, the diamino-monocarboxylic acids, diamino-dicarboxylic acids and lactams having 3 to 12 carbon atoms in the ring.

The amino acids which may be used in the instant invention may be either optically active or inactive and include monoamino-monocarboxylic acids such as alanine, isoleucine, 3-aminobutyric acid, 3-aminopropionic acid, 3-amino-2-methyl propionic acid, phenyl alanine, p-aminobenzoic acid, methionine, $\omega$-amino acids generally, etc.; monoamino-dicarboxylic acids such as aspartic acid and glutamic acid; diamino-monocarboxylic acids such as lysine and ornithine; diamino-dicarboxylic acids such as lanthionine; and lactams such as $\epsilon$-caprolactam, $\beta$-methyl-$\beta$-butyrolactam, $\alpha,\beta$-dimethyl-butyrolactam, $\alpha,\alpha',\beta$-trimethylbutyrolactam, $\beta$-carbomethoxy-butyrolactam, $\beta$-phenyl-$\beta$-propiolactam, $\beta$-methyl-$\beta$-caprolactam, $\beta$-methyl-$\beta$-valerolactam, $\beta$-ethyl-$\beta$-valerolactam, 2-pyrrolidone, 6-methyl-2-piperidone, 3-methylcaprolactam and 7-methylcaprolactam. The amino acids may be substituted with inert substituent groups as alkyl, nitro, halogens, etc. and may contain one or more hetero atoms which do not interfere with the esterification reaction, and, where applicable, the subsequent phosgenation. Mixtures of amino acids may be used. The diaminomonocarboxylic acids disclosed in French Pat. No. 1,351,368 may be used. Amino acids occur widely in nature and a number of synthesis methods are available for their production from inexpensive raw materials. Thus the addition of ammonia to an unsaturated acid may be used to produce inexpensive amino acids for use in the instant invention. When a lactam is used as the amino acid, desirably water (preferably at least one mole per mole of lactam) is added along with the sulfonic acid component to facilitate opening the ring. An undue excess of water is to be avoided since it must be removed during the esterification. The lactam may be first added in contact with the water-acid mixture and then the alkanolamine added along with an inert organic liquid and an azeotropic agent and the ester prepared as above. Alternatively, all the reactants may be charged initially, the mixture heated without removal of water for a sufficient time to open the ring, and then the water is removed causing esterification to proceed. Other variations may also be used, as charging the lactam after the alkanolamine is charged, or initially charging all the materials except the azeotropic agent which is added after ring opening.

Where the acyloxyalkylamine sulfonic acid salt is to be converted to the corresponding isocyanate, the conversion is carried out with phosgene or other carbonyl dihalide. The phosgene may be employed in either liquid or gaseous form. In the phosgenation reaction, the acyloxyalkylammonium sulfonate or sulfonic acid salt is dispersed in an inert, liquid reaction medium, phosgene added, preferably in excess of that needed to react quantitatively with the amino groups, and the temperature of the reaction medium maintained from about 60° C. to about 225° C. The molar ratio of phosgene: acyloxyalkylammonium sulfonate may be from 1.1:1 to 10:1 and preferably is at least 2:1. Suitable liquid reaction media include aromatic hydrocarbons, chlorinated aromatic hydrocarbons, chlorinated aliphatic hydrocarbons, chlorinated alicyclic hydrocarbons, etc. The phosgenation may also be carried out in steps. The ester reaction product of the acid—or amino acid-alkanolamine sulfonate reaction may be used as such for the phosgenation i.e., without any separation as heretofore noted, or, if desired, the acyloxyalkylammonium sulfonate may first be purified and the purified product phosgenated.

Representative uses of the acyloxyalkylamine sulfonic acid salts of the invention are disclosed supra. The isocyanates produced therefrom may be used as cross-linking agents for polymers containing active containing active hydrogen groups, may be reacted with low molecular weight polymers containing active hydrogen groups such as hydroxyl-terminated polyesters or polyethers to produce polyurethanes, and may be added to polymeric compositions to improve the adhesion thereof to a variety of substrates, particularly metallic substrates. They are also useful as intermediates in producing other novel compounds useful as modifying agents for textiles, cellulose, starch, polyvinyl alcohol, algin, copolymers of hydroxyalkyl esters of unsaturated acids, etc.

The following examples are by way of illustration and not of limitation. All parts and percentages are by weight unless otherwise specified. All temperatures are in degrees Centigrade.

EXAMPLE 1

Preparation of 2-aminoethyl 6-aminocaproate, bis-benzenesulfonic acid salt

A 4-necked, Morton-type (indented) flask is fitted with a mechanical stirrer, a thermometer, a reflux condenser, and a pressure equalizing dropping funnel. The flask is charged with 180 g (10.0 moles) of water which is then heated to 90° C. Keeping the temperature between 90° and 110°, 530 g (3.00 mole) of benzenesulfonyl chloride are added gradually over a one-hour period to hydrolyze it to benzenesulfonic acid and hydrogen chloride. Toward the latter part of the addition, vigorous evolution of hydrogen chloride is observed. After stirring at 100° for 0.5 hr., the mixture is cooled to 50°, and 113.2 g (1.00 mole) of $\epsilon$-caprolactam and 61.1 g (1.00) of 2-aminoethanol are charged. The mixture is then held at 115° for 6 hours to hydrolyze the caprolactam to aminocaproic acid. Most of the water is then stripped off under reduced pressure (16 mm.) with heating on the steam bath. Then the reflux condenser is replaced by a Dean-Stark water separator trap and condenser, 180 g of xylene are added, and the mixture is heated under reduced pressure so as to reflux at 110° (ca. 328 mm. Hg. pressure). After azeotroping off water for 8–10 hours, the esterification is essentially complete. The product can be isolated by crystallization from isopropanol, m.p. 142°–143°. Anal. Calc'd for $C_{20}H_{30}N_2O_8S_2$: C, 48.96; H, 6.16; N, 5.71; S, 13.07. Found: C, 48.67; H, 6.10; N, 5.25; S, 11.99.

EXAMPLE 2

Preparation of 2-Isocyanatoethyl 6-isocyanatocaproate

It is not necessary to isolate and purify the sulfonic acid salt of the aminoester from the crude reaction mixture prior to phosgenation and conversion to the isocyanate. Instead, the crude esterification reaction mixture, along with an excess sulfonic acid, may be reacted with phosgene directly to produce the isocyanate.

Thus, the product of Example 1, as a suspension in the xylene diluent employed for the esterification, is cooled to 100°, and phosgene is passed in at the rate of 1 mole per hour. After approximately 3-4 hours, the suspended melt is transformed into a crystalline solid. After an additional 1-2 hours of phosgenation at 100°, 1.5 ml. of dimethylformamide is added and the temperature is raised to 115°. Phosgenation is continued for about 8 hours more until the mixture is practically free of suspended solid. The yield of the isocyanate, 2-isocyanatoethyl 6-isocyanatocaproate, is (according to vapor phase chromatographic analysis) typically 70-90% largely depending upon how complete the esterification reaction had been. The benzenesulfonyl chloride is produced in nearly quantitative yield.

EXAMPLE 3

Preparation of 2-Aminoethyl Methacrylate, 3,4-Dichlorobenzenesulfonic Acid Salt

A 1-liter flask containing 1.10 moles of 3,4-dichlorobenzenesulfonic acid, 1.00 mole of methacrylic acid, 1.00 mole of ethanolamine, 270 g of xylene, and 1 g of diphenylphenylenediamine polymerization inhibitor, is fitted with a mechanical stirrer, a thermometer, a Dean-Stark water separator trap and condenser, and is set up for reduced pressure azeotropic distillation.

Water is azeotroped off at 80° (ca. 110 mm. Hg. pressure) for 17-20 hours until the esterification is essentially complete. This reaction mixture is suitable for reaction with phosgene to prepare isocyanatoethyl methacrylate.

If desired, the pure 2-aminoethyl methacrylate, 3,4-dichlorobenzenesulfonic acid salt may be isolated and purified by recrystallization from a xylene-isopropanol mixture, m.p. 147°. Anal. Cal'd for $C_{12}H_{15}NO_5Cl_2S$: C, 40.45; H, 4.21. Found: C, 40.98; H, 4.36.

EXAMPLE 4

Preparation of 2-Isocyanatoethyl Methacrylate

To the reaction mixture of Example 3 is added 25 g of 1,2-dichloroethane and 3.5 g of dimethylformamide. Keeping the temperature at 70°, phosgene is passed in at the rate of 0.5 mole/hr. for 6-8 hours, adding additional dimethylformamide as follows: 0.05 mole at 1.0 hour, 0.01 mole at 2.0 hr., and 0.03 mole at 3.0 hr. At the end of this period, the mixture is sparged with dry air at 120° for 4 hours. The product is isolated by careful functional distillation through a short Vigreaux column. The cut boiling 65°-85° (1-2 mm.) corresponds to pure (99%) 2-isocyanatoethyl methacrylate. A later cut, b.p. 85°-130° (1-2 mm.) is 3,4-dichlorobenzenesulfonyl chloride.

EXAMPLE 5

Preparation of 2-Isocyanatoethyl Methacrylate

This example illustrates the phosgenation of pure 2-aminoethyl methacrylate, p-chlorobenzenesulfonic acid salt.

A 1-liter, 5-necked flask is fitted with a mechanical stirrer, a gas inlet tube, and a thermometer. The flask was charged with 162 g (0.50 mole) of pure 2-aminoethyl methacrylate, p-chlorobenzenesulfonic acid salt, 250 g of heptane, 50 g of 1,2-dichloroethane, 3.5 g of dimethylformamide, and 1 g of diphenylphenylenediamine.

Air (20 ml/min) and phosgene (0.5 mole/hr.) are passed into the stirred mixture at 70° until the phosgenation is complete (ca. 6 hrs.) Vapor phase chromatographic analysis at this time indicates the yield of 2-isocyanatoethyl methacrylate to be essentially quantitative.

Table I

Additional Examples of Sulfonic Acid Salts of Aminoalkyl Esters

In Table I are given the melting points, and elemental analyses of representative aminoalkyl ester sulfonic acid salts prepared by direct esterification of carboxylic acids (or anhydrides wherein indicated) with the sulfonic acid salt of the alkanolamine. All of the reactions are carried out using an inert diluent to aid in the removal of water, while operating at the reflux temperature of the diluent, and at atmospheric or lower pressure. (Previous examples have demonstrated that it is not necessary to operate at atmospheric pressure, and that any pressure giving a convenient boiling point for a particular diluent may be used.) In the examples in Table I, an excess of sulfonic acid is employed (10% in most examples), and the carboxylic acid (or anhydride) is added directly to the mixture, except for the first entry (2-aminoethyl 6-aminocaproate bismethanesulfonic acid salt) where the amino acid is generated in situ by hydrolysis of caprolactam. Sulfonic acid is either added as the free acid or made in situ by hydrolysis of the sulfonyl chloride as, for example, was illustrated in Example 1. The reactions in Table I are run at temperatures ranging from 80° C. to 180° using as diluents benzene, toluene, xylene, and mixtures of xylene and sulfolane. In the case of the unsaturated esters, the sulfonic acid, where generated in situ, from the hydrolysis of sulfonyl chloride, is first dried azeotropically with the diluent to insure the removal of hydrogen chloride. (The reference to an excess of a sulfonic acid, in the specification and in the claims, refers to that quantity of a sulfonic acid which should be present during the esterification reaction and which is in excess of that required to form a sulfonic acid salt with the alkanolamine and with the amino acid (or lactam) when present. Ordinarily, this excess will vary between about 5 to 200 mole percent and, more preferably, from about 10 to 100 mole percent).

TABLE I

| | | | | | Elemental Analysis | | | | |
|---|---|---|---|---|---|---|---|---|---|
| | Carboxylate Species Used as Starting | | Melting | (Calculated over Found) | | | Esterification | | |
| Ex. | Material | Product | Point | C | H | N | Temp. (Pressure) | Diluent |
| 6 | caprolactam | bis-methanesulfonic acid salt of 2-aminoethyl 6-aminocaproate | 115°-116° | 32.77<br>32.48 | 7.15<br>7.08 | 7.65<br>7.00 | 118° (atmospheric) | 35/65 (w/w) toluene/xylene |

TABLE I-continued

Additional Examples of Sulfonic Acid Salts of Aminoalkyl Esters

| Ex. | Carboxylate Species Used as Starting Material | Product | Melting Point | *Elemental Analysis (Calculated over Found) C | H | N | Esterification Temp. (Pressure) | Diluent |
|---|---|---|---|---|---|---|---|---|
| 7 | acrylic acid | benzenesulfonic acid salt of 2-aminoethyl acrylate | 115° | 42.93 / 43.02 | 4.55 / 4.58 | 4.55 / 4.50 | 80° (atmospheric) | benzene |
| 8 | methacrylic acid | benzenesulfonic acid salt of 2-aminoethyl methacrylate | 135° | 50.17 / 50.50 | 5.92 / 5.87 | | 80° (atmospheric) | benzene |
| 9 | methacrylic acid | 2-naphthalenesulfonic acid salt of 2-amino-ethyl methacrylate | 155° | 56.97 / 56.64 | 5.64 / 5.58 | | 111° (atmospheric) | toluene |
| 10 | methacrylic acid | p-chlorobenzenesulfonic acid salt of 2-aminoethyl methacrylate | 162° | 44.79 / 44.66 | 4.98 / 5.07 | | 80° (110 mm.) | xylene |
| 11 | methacrylic acid | 2,5-dichlorobenzene-sulfonic acid salt of 2-aminoethyl methacrylate | 153° | 40.45 / 40.81 | 4.21 / 4.32 | | 80° (110 mm.) | xylene |
| 12 | p-aminobenzoic acid | bis-benzenesulfonic acid salt of 2-amino-ethyl p-aminobenzoate | 233° | 50.81 / 51.76 | 4.84 / 4.95 | 5.65 / 6.01 | 140°–160° (atmospheric) | 50/50 (w/w) xylene/sulfolane |
| 13 | terephthalic acid | bis-benzenesulfonic acid salt of bis-2-aminoethyl terephthalate | 258° | 50.70 / 50.81 | 4.93 / 5.03 | 4.93 / 5.02 | 145°–180° (atmospheric) | 50/50 (w/w) xylene/sulfolane |
| 14 | phthalic anhydride | bis-benzenesulfonic acid salt of bis-2-aminoethyl phthalate | 187° | 50.70 / 50.80 | 4.93 / 4.86 | 4.93 / 4.99 | 140° (atmospheric) | xylene |
| 15 | maleic anhydride | bis-benzenesulfonic acid salt of bis-2-aminoethyl fumarate | 191° | 46.33 / 46.91 | 5.01 / 5.21 | 5.40 / 5.17 | 140°–165° (atmospheric) | xylene |

*C = Carbon
H = Hydrogen
N = Nitrogen

What is claimed is:

1. An alkyl, cycloalkyl, alkaryl, aralkyl, or halogen-substituted alkyl, cycloalkyl, alkaryl, or aralkyl sulfonic acid salt of 2-aminoethyl methacrylate or 2-aminoethyl acrylate.

2. Composition of matter according to claim 1 wherein the salt is the 3,4-dichlorobenzenesulfonic acid salt of 2-aminoethyl methacrylate.

3. Composition of matter according to claim 1 wherein the salt is the benzenesulfonic salt of 2-aminoethyl methacrylate or 2-aminoethyl acrylate.

4. Composition of matter according to claim 1 wherein the salt is the 2-napthalenesulfonic acid salt of 2-aminoethyl methacrylate.

5. Composition of matter according to claim 1 wherein the salt is the p-chlorobenzenesulfonic acid salt of 2-aminoethyl methacrylate.

6. Composition of matter according to claim 1 wherein the salt is the 2,5-dichlorobenzenesulfonic acid salt of 2-aminoethyl methacrylate.

7. An alkyl, cycloalkyl, alkaryl, aralkyl, or halogen-substituted alkyl, cycloalkyl, alkaryl, or aralkyl sulfonic acid salt of a primary amino alkyl ester of an aliphatic dicarboxylic acid, an aromatic dicarboxylic acid, acrylic acid, or methacrylic acid.

8. A sulfonic acid salt according to claim 7 wherein the amino alkyl ester is 2-aminoethyl methacrylate, or 2-aminoethyl acrylate.

* * * * *